United States Patent [19]

Albeck et al.

[11] Patent Number: 4,923,697

[45] Date of Patent: * May 8, 1990

[54] ANTIOXIDANT COMPOSITIONS AND METHODS

[75] Inventors: Michael Albeck; Shlomo Grossman, both of Ramat Gan, Israel

[73] Assignee: Bar-Ilan University, Ramat-Gan, Israel

[*] Notice: The portion of the term of this patent subsequent to Aug. 15, 2006 has been disclaimed.

[21] Appl. No.: 932,702

[22] Filed: Nov. 19, 1986

Related U.S. Application Data

[63] Continuation-in-part of Ser. No. 846,599, Mar. 31, 1986, Pat. No. 4,851,325, which is a continuation-in-part of Ser. No. 726,540, Apr. 25, 1985, abandoned.

[51] Int. Cl.⁵ ............................................. A61K 35/78
[52] U.S. Cl. ................................................. 424/195.1
[58] Field of Search .................................... 424/195.1

[56] References Cited

U.S. PATENT DOCUMENTS

| | | | |
|---|---|---|---|
| 2,098,254 | 11/1937 | Mattill et al. | 426/546 |
| 2,282,808 | 5/1942 | Musher | 424/195.1 |
| 2,382,242 | 8/1945 | Lindow et al. | 426/72 |
| 3,628,971 | 12/1971 | Karchmar | 426/546 |
| 3,883,505 | 5/1975 | Hamuro | 536/124 |
| 3,948,801 | 4/1976 | Braddon et al. | 252/400 A |
| 4,011,206 | 3/1977 | Higginbotham | 426/656 |
| 4,075,406 | 2/1976 | Melaja et al. | 536/1 |
| 4,154,822 | 5/1979 | Polimeni et al. | 536/4 |
| 4,321,360 | 3/1982 | Blount | 536/1 |
| 4,352,746 | 10/1982 | Bracco et al. | 252/398 |
| 4,361,697 | 11/1982 | Dobberstein et al. | 536/128 |
| 4,380,506 | 4/1983 | Kimura et al. | 252/398 |
| 4,499,267 | 2/1985 | Scifoni | 44/51 |
| 4,511,559 | 4/1985 | Szendrei et al. | 514/54 |
| 4,525,306 | 6/1985 | Yajima | 260/428.5 |
| 4,536,496 | 8/1985 | Shimizu et al. | 514/54 |
| 4,569,839 | 2/1986 | Grollies et al. | 424/74 |

FOREIGN PATENT DOCUMENTS

| | | |
|---|---|---|
| 2209856 | 8/1973 | Fed. Rep. of Germany . |
| 3207005 | 9/1982 | Fed. Rep. of Germany . |
| 1573315 | 7/1969 | France . |
| 2229388 | 12/1974 | France . |
| 2484836 | 12/1981 | France . |
| 102809 | 6/1982 | Japan . |
| 42686 | 3/1983 | Japan . |
| 219384 | 12/1984 | Japan . |
| 8601713 | 3/1986 | PCT Int'l Appl. . |

OTHER PUBLICATIONS

CTFA Cosmetic Ingredient Dictionary, p. 298, Monograph or Spinach Extract.
Medycyna Weterynaryjna, No. 7, Roh XXVIII, pp. 430–433 (1972).
CA, vol. 95, p. 543 (1981) 95:113703m.
Pat. Abstracts of Japan, Unexamined Appln. C, vol. 4, No. 98, (1980); The Patent Office Japanese Government, p. 134 C 18–Kokai–No. 55-62 005 (Kurorera).
Patent Abstracts of Japan, Unexamined Applns., C Section, vol. 1, No. 27, (1977); The Patent Office Japanese Government–p. C 3969–Kokai–No. 51-142 514 (A. Fukuda).
Patent Abstracts of Japan, Unexamined Applns., C. Section, vol. 1, No. 48, (1977); The Patent Office Japanese Government–p. 6 C 77–Kokai–No. 52—3 835 (Jef-'cee Foods).
Patent Abstracts of Japan, Unexamined Applns. C Field, vol. 8, No. 145, (1984); The Patent Office Japanese Government–p. 57 C 232–Kokai–No. 59-51 763 (Nihon Rikagaku Yakuhin).
Journal of Food Science, vol. 36, (1971), Chicago, pp. 571, 572–(A. Pinsky et al.)-Totality.
Patent Abstracts of Japan, Unexamined Applications C Field, vol. 7, No. 122, (1983); The Patent Office Japanese Government–p. 136 C 168–Kokai–No. 58-42 686 (Hasegawa Koryo K.K.).

*Primary Examiner*—John W. Rollins
*Attorney, Agent, or Firm*—Hedman, Gibson, Costigan & Hoare

[57] ABSTRACT

A water soluble antioxidant is obtained from plants of the Order Chenopodiales which has the capability of lowering the peroxide level of the skin. The antioxidant is obtained by a process which comprises extraction of the plant tissue with water and to thereafter chromaographically separating the antioxidant component.

24 Claims, 11 Drawing Sheets 4,923,697

ANTIOXIDANT COMPOSITIONS AND METHODS

CROSS REFERENCE TO RELATED APPLICATION

This application is a continuation-in-part of Ser. No. 846,599 filed Mar. 31, 1986, now U.S. Pat. No. 4,857,325, which is a continuation-in-part of Ser. No. 726,540 filed April 25, 1985 now abandoned.

FIELD OF THE INVENTION

This invention relates to novel compositions, substances and methods that may be used for cosmetics, food preservation or therapeutic purposes.

BACKGROUND OF THE INVENTION

The use of specific materials to inhibit or prevent oxidative degradation of natural or synthetic materials is well known. Many of the materials utilized for this purpose are insoluble in water and toxic to mammals at both high and low levels. Examples of such materials are BHA (butylated hydroxy anisole); BHT (butylated hydroxy toluene); propyl gallate; and alpha-tocopherol. It is known that natural antioxidants are widely distributed in plant tissues. Certain of these antioxidants have been obtained in crude form and have been shown to have an effect on commercial soybean lipoxygenase [J. Food Science, 36: 571 (1971)]. Japanese patent application SHO 58-42686 discloses an alkali-organic solvent extraction process for obtaining an antioxidant from white pepper powder. The Polish publication Medycyna Weterynaryjna 28: 430–433 describes the extraction with boiling distilled water of dried hay or Urtica. The resulting extract was used as an antioxidant for fish meal; it is stated that the extract may be stored until use for not more than 48 hours at 4° C.

The applicants have described in the parent application, antioxidants which are stable under ambient conditions for extended periods, and which may be obtained by water extraction of plant tissues, and that such antioxidants are absorbed percutaneously, and exert an antioxidant effect on the outer and inner layers of the skin. These effects are advantageously obtained when the antioxidant is applied to the skin as a dispersion in a hydrophilic or hydrophobic base. The cosmetic result of the application of the antioxidant comprises a softening of the skin which is detectable by touching with the fingertips. In addition, it was found that the peroxide level of the skin is reduced by application of the antioxidants and that the antioxidants may also be utilized for the preservation of food in place of, for example, BHT or BHA.

The particular plant tissues (e.g. the leaves) mentioned in the parent application, from which the water-soluble antioxidants were extractable, were Spinacia (*Spinacia oleracea*: spinach), Trifolium (clover), Medicago (*Medicago sativa*: alfalfa), Zea (*Zea mays*: corn), Nicotiana (*Nicotiana tabacum*: tobacco), Pennisetum and Allium (onion and garlic). In accordance with the present invention, it has been discovered that other specific species may also be used as a source of the antioxidants.

SUMMARY OF THE INVENTION

The invention comprises compositions and methods which relate to water soluble antioxidants, derived from plant tissues, which are capable of being absorbed into mammalian skin where they reduce the peroxide level. The antioxidants may also be used for food preservation and for therapeutic purposes.

Accordingly, it is a primary object of the invention to provide antioxidant materials prepared from hitherto undisclosed sources, as well as a process for preparing such substances.

It is still a further important object of the invention to provide a cosmetic composition and methods which may be used for application to the skin.

It is also an object of the invention to provide a composition that may be absorbed through the skin to provide an antioxidant effect.

It is a further object of the invention to provide compositions and methods for therapeutic purposes.

It is yet a further object of the invention to provide compositions and methods for preventing oxidation in foods.

Other objects of the invention will appear from the description which follows.

These objects are achieved in accordance with the present invention, which provides a material selected from water soluble extracts prepared from plant tissue, and fractions separable from said extracts by chromatography, wherein said tissue is preferably obtained from a plant of the order Chenopodiales which contains seven families: Chenopodiaceae; Phytolaccaceae; Amaranthaceae; Nyctaginacea; Aizoaceae; Portulacaceae; and Caryophyllaceae, said material having the first and second, most preferably also the third and/or the fourth of the following characteristics, namely:

(i) it is an antioxidant;
(ii) it is stable for an extended period of time, at least in the dry state, at ambient temperature and pressure;
(iii) it is absorbed through the skin;
(iv) it lowers the peroxide level of the skin.

Chenopodiaceae is for the purposes of the present patent application defined as the plant family by that name known to one skilled in the botanical art. Examples of the family Chenopodiaceae within the scope of this definition are Spinacia, e.g. *Spinacia oleracea* Atriplex, e.g. "Mountain Spinach" (*Atriplex hortensis*), otherwise known as "Orach", and Beta, e.g. the beet varieties included within Beta vulgaris. Aizoaceae is for the purposes of the present patent application defined as the plant family by that name known to one skilled in the botanical art, an example being Tetragonia, e.g. "New Zealand Spinach" (*Tetragonia expansa*).

DETAILED DESCRIPTION OF THE INVENTION

Figure 1:
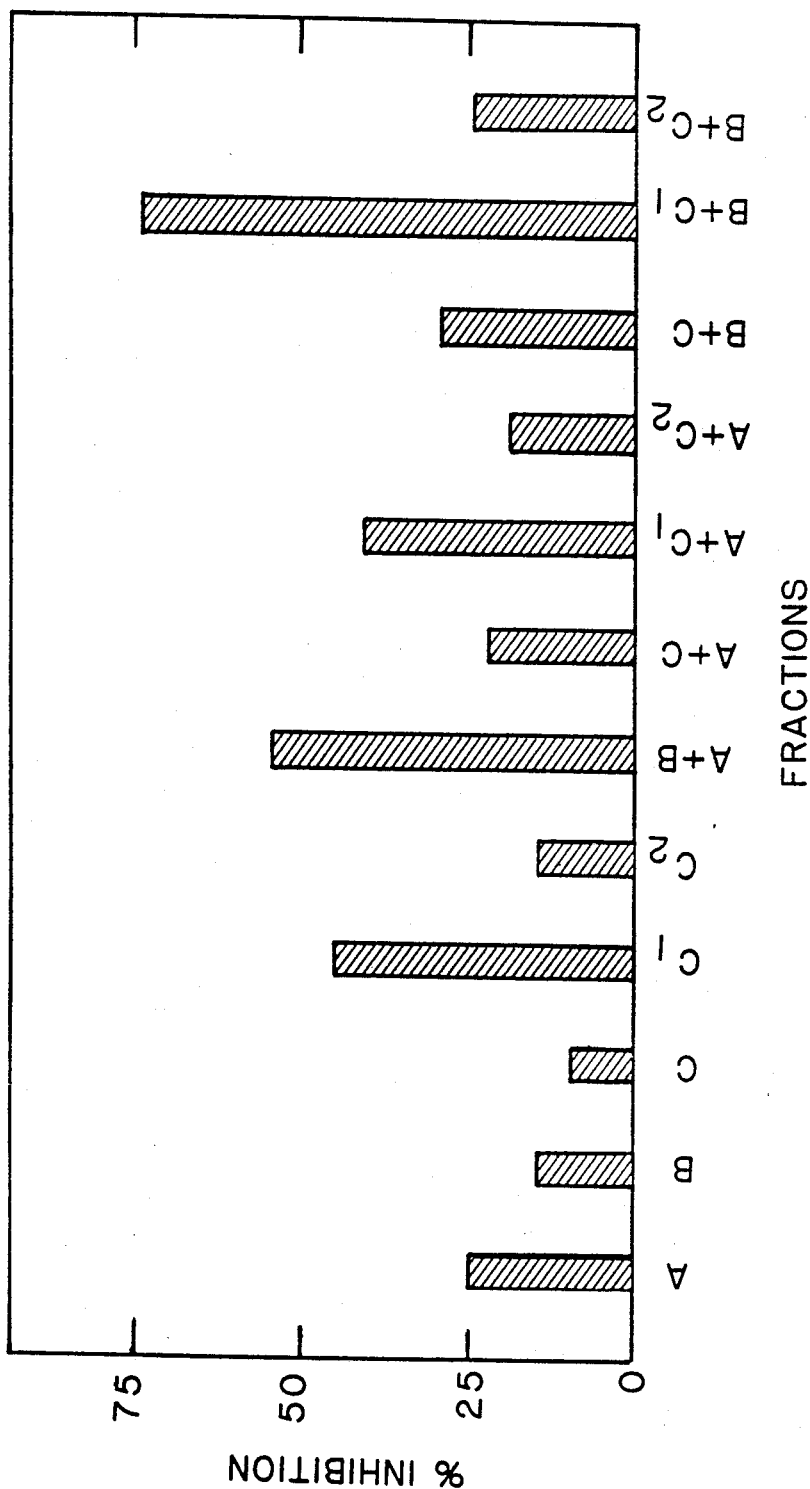
FIG. 1 is a chart which shows the synergistic results of the use of selected antioxidant fractions.

The present invention provides cosmetic compositions for application to the skin. These compositions comprise a cosmetically acceptable carrier and an effective amount of a water soluble extract, from plant tissue such as plant leaves and stems, which is capable of being absorbed through the skin and lowering the peroxide level of the skin.

The plants which were especially utilized in the parent application as a source of the water soluble extract included the plant tissues of selected species such as the stems and green leaves selected from the group consisting of Spinacia, Trifolium, Medicago, Zea, Nicotiana, Pennisetum and Allium. On the other hand, the present invention uses plant tissues obtained from members of the plant order Chenopodiales (as defined herein). The antioxidant effect is determined by the thiobarbituric acid (TBA) test. This test is described in Food Res. 23: 620 (1958). Generally, the level of peroxide in the skin may be determined by assay of a sample of untreated skin which is peeled from a test animal. A preweighed sample from 10 to 50 mg. is homogenized in 0.2M phosphate buffer pH 6.5 and centrifuged. The supernatant is collected and the peroxide level is determined using the TBA test. A sample of the skin from the same animal which has been treated with the antioxidant according to the invention is also peeled and the peroxide level is determined. A reduction in the peroxide level of about 35%, when an antioxidant according to the invention is applied at 0.5% w/w dispersion in a petrolatum base, is the criterion for determining if a given plant extract is a useful antioxidant.

The cosmetically acceptable carrier may be any liquid or semisolid type of material that is compatible with the plant extract and non-irritating to the skin.

The antioxidant may be extracted from plant material using a plant to water ratio in the range of 0.5:100 to 1.0:0.5 (w/v), preferably 2:1 (w/v), after comminution of the plant material. This may be carried out at temperatures within the range of about 4° to about 100° C., preferably at about 25° C., using a blender, grinder or any other type of apparatus which will fragment the cell walls. A especially preferred extraction process comprises boiling the whole plant leaves in water for 30-90 minutes or longer. The extracted plant material is separated using filtration, centrifugation, decantation, froth flotation, or any other conventional method used for separating a solid from a liquid.

The crude antioxidant may be used as obtained from the plant, either in dilute form or as an aqueous mixture or as a purified extract. Generally, it is preferred to separate the aqueous extracting medium from the dissolved antioxidant by evaporation or lyophilization of the liquid portion to provide a dry, water soluble antioxidant. The crude extract may be purified using chromatographic techniques.

Generally, the powder is dissolved in water to form a 10 to 30% w/w solution which is applied to the top of the column and is allowed to move through the column. The various fractions are eluted using water as washing medium and the various fractions are separately collected. The individual fractions may be further purified by a second chromatographic procedure using a packing medium having a smaller pore size than in the preceding step.

Sephadex G-25 may be utilized as a chromatographic column separation medium to resolve the crude extract from spinach into a brown fraction, a yellow fraction and an orange fraction. The orange fraction may be extracted with water and further separated chromatographically using a Sephadex G-10 column. Sephadex G-25, medium grade, is dextran that has been cross-linked with epichlorohydrin and has a pore size of 50–150 um. Sephadex G-10 is dextran that has been cross-linked with epichlorohydrin and has a pore size of 40–120 um. Thin layer chromatography is utilized to separate a yellow fraction from the orange fraction. The Sephadex materials are described in Gell Filtration Theory and Practice, Pharmacia pp. 1–64, which is incorporated by reference.

The applicants have isolated several different active antioxidant fractions, which may be used separately or in combination. Several of the combined fractions have been shown to have higher activity than the crude fraction. The relative amounts of the brown, orange and yellow fractions may be varied to give optimum results. Generally, any two fractions may be used at weight ratios of 1:99 to 99:1, based on the total weight of the combined fractions. However, it is also within the scope of the invention to combine together more than two fractions.

For cosmetic use, the total amount of antioxidant that may be used may vary from about 0.005 to about 5% preferably from about 0.1 to about 1%, by weight, of the total weight of the product.

The nature of the cosmetic base is not critical and any suitable cosmetic cream or lotion may be utilized.

The antioxidant may be used in lipstick, face cream, body lotion, moisture creams, burn remedies containing local anaesthetics such as 1% benzocaine and the like. The antioxidant has a protective effect against damage to the skin that is induced by ultraviolet light having a frequency in the range of 200–340 nm. Therefore, the antioxidant may be applied to the skin, to prevent damage caused by radiation from natural sources such as the sun, or from artificial sources, either alone or in combination with sunscreen agents such as PABA.

When foods are preserved with the antioxidants of the invention, an amount of the latter effective to prevent oxidation of the fat comprised in the food should be used. Generally, from about 0.001 to about 1%, preferably from about 0.005 to about 0.1% by weight of the foodstuff may be used, depending on the foodstuff and the type of oxidative activity which is to be inhibited.

More particularly, foodstuffs which contain fats or oils comprising fatty acids or their esters, either saturated or unsaturated, may be preserved using the water soluble antioxidants according to the invention. The fatty acids are well know and are listed in Noller, Textbook of Organic Chemistry, 2nd Ed. pp. 108–113 and 138–146 (1958), which is incorporated by reference. Typical foodstuffs, or fats and oils contained therein, include soybean oil, corn oil, cottonseed oil, olive oil, butter, margarine, dairy products, ice cream, frozen vegetables, soups, fried foods and the like.

Both crude and purified antioxidants in accordance with the invention are stable to high temperature, e.g. at the temperature of boiling water for 30 minutes. Moreover, they have good stability for extended periods under ambient conditions. By way of example, the crude extract from spinach in powder fpr, jad been kept for more than one year at room temperature, without any loss in its antioxidant activity.

Toxicity studies have been carried out using both crude and purified fractions, and no pathological changes have been detected when the materials have been administered by injection or orally.

The antioxidants have also been shown to be effective in inhibiting tumors such as fibrosarcoma induced by methylcholanthrene and skin cancer such as squama cell carcinoma which is induced by dimethylbenzoicanthrene and 4B-phorbol 12-myristate-13-acetate, and ultraviolet light. For this purpose the antioxidants may be administered at dosages within the range of from about 20 to about 500 mg./kg. of body weight, either orally, rectally or parenterally, e.g. by injection. The invention accordingly includes pharmaceutical compositions which comprise the antioxidants of the invention, together with an inert diluent or carrier. In the case of the inhibition of skin cancer, the antioxidants are administered topically.

DESCRIPTION OF THE PREFERRED EMBODIMENTS

Leaves from *Spinacia oleracea* were homogenized with $H_2O$ at 25° C. at a ratio of 2:1 (w/v) in a Waring blender for 5 minutes. The resulting homogenate was filtered through cheesecloth and then centrifuged at $15000 \times g$ for 10 minutes. The supernatent was collected and lyophilized.

The isolation and purification of antioxidant fractions from the crude homogenate preparation was achieved through gel filtration followed by preparative TLC or HPLC. 1 g. of the lyophilized powder of the crude homogenate was dissolved in 5 ml. $H_2O$ and after centrifugation at $20000 \times g$ for 10 minutes, the supernatant was applied to a Sephadex G-25 column (40 cm. $\times$ 2.5 cm.), equilibrated and eluted with water. Fractions of 5 ml. were collected and each was assayed fro antioxidant activity. The active fractions (A, B and C) were pooled (fraction A has a brown, B a yellow and C an orange color), and lyophilized fraction C was further purified. The lyophilized material of fraction C was dissolved in water to form a 20% solution (m/v), centrifuged at $20000 \times g$ for 10 minutes, and the supernatant was chromatographed on a Sephadex G-10 column (40 cm. $\times$ 2.5 cm.), and equilibrated with water. Fractions were collected, pooled and lyophilized as before. Lyophilized fraction C("$C_1$") was dissolved in a minimum amount of water, applied to 0.2 mm. silica gel plates (DC-Karten SIF, Riedel-Dollaen AG., sleeze-Hanover) and developed in 30:60 v/v $H_2O$-ethanol. The active fraction was identified by its weak (pale) yellow color and was extracted from the silica gel plate with water and lyophilized.

Figure 7:
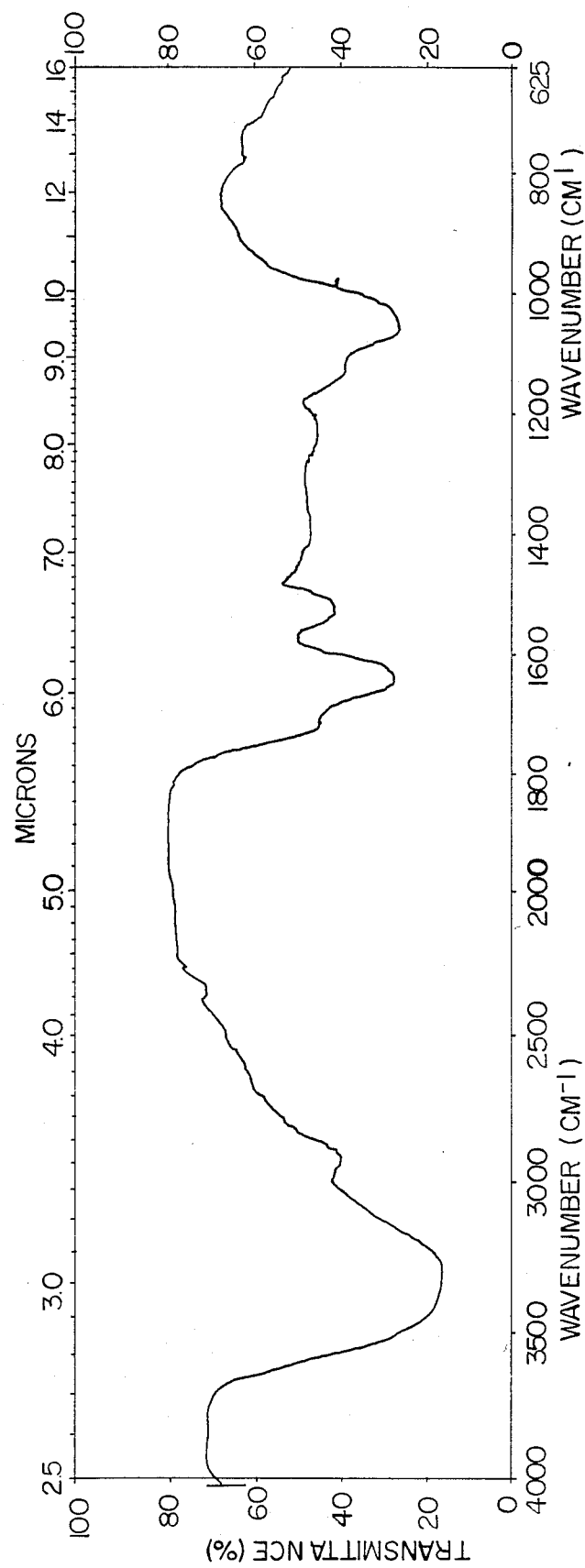
FIG. 7 shows an infrared curve of the antioxidant fraction $A_1$ of the invention, isolated from spinach.

A further purification was carried out using DEAE cellulose (small size). The fraction identified hereinabove as A was dissolved in water and passed through a 5 cm. $\times$ 1 cm. column packed with DEAE cellulose (small size). (Alternatively, the column packing may be Ecteola, a condensation product of cellulose with epichlorohydrin and triethanolamine having a capacity of 0.3 to 0.4 meg./g. and a particle size 0.05–0.2 mm.) The column was equilibrated with water that was acidified to a pH of 5–6 with 0.2N HCl. The column was eluted with a solution of HCL, pH 2.0 and the eluted material was recovered as a powder by vacuum evaporation. A pure product ($A_1$) was obtained which had the infrared curve of FIG. 7. The powder was further purified by dissolving in water at a concentration of 20 ug./ml. and passing through a high pressure liquid chromatography silica 60 column (250 mm. $\times$ 4 mm.) with a 90:10 solution of water:acetonitrile applied at a rate of 0.5 ml./min. A fraction was obtained which had a retention fraction at 5.4 nanometers (UV absorption).

EXAMPLE 1

From the crude extract of the plant material, 3 antioxidant active fractions (A, B and C) were obtained following the first step of purification. Fraction C was further purified on a column packed with Sephadex G-10 and two other active fractions were obtained by elution with water ($C_1$ -dark brown and $C_2$ -yellow orange). Fraction $C_1$ was finally purified using HPLC. In studying the antioxidant activity of the crude plant extracts and the isolated fractions, both the inhibition of linoleate oxidation by lipoxygenase and the inhibition of auto-oxidation of peroxides were used as criteria for antioxidant activity.

The antioxidant fractions exhibited synergistic activity. The synergism obtained with the natural isolated antioxidants is shown in FIG. 1, which depicts the percentage inhibition on lipid oxidation of 1 mg. each of single purified antioxidant fractions, as well as the analogous percentage inhibition using combinations of 0.5 mg. each of two such fractions. By way of example, it may be seen that this synergism increased the potency produced by the compounds from 167% ($B+C_2$) up to 250% ($A+B$), without increasing the total antioxidant content.

Since lipid peroxidation catalyzed by hemeproteins is a basic deteriorative and pathological reaction, the effectiveness of the isolated fractions to prevent such peroxidation was followed. It was found that the isolated fractions prevent such peroxidation induced by haemoglobin, cytochrome C and myoglobin, in a similar way to the inhibition of lipoxygenase-induced oxidation.

The purified antioxidant fractions retained their antioxidative activities for months, without any loss, when kept at room temperature. Moreover, boiling the purified antioxidants for up to 30 minutes, did not reduce their antioxidant capacity.

Figure 3:
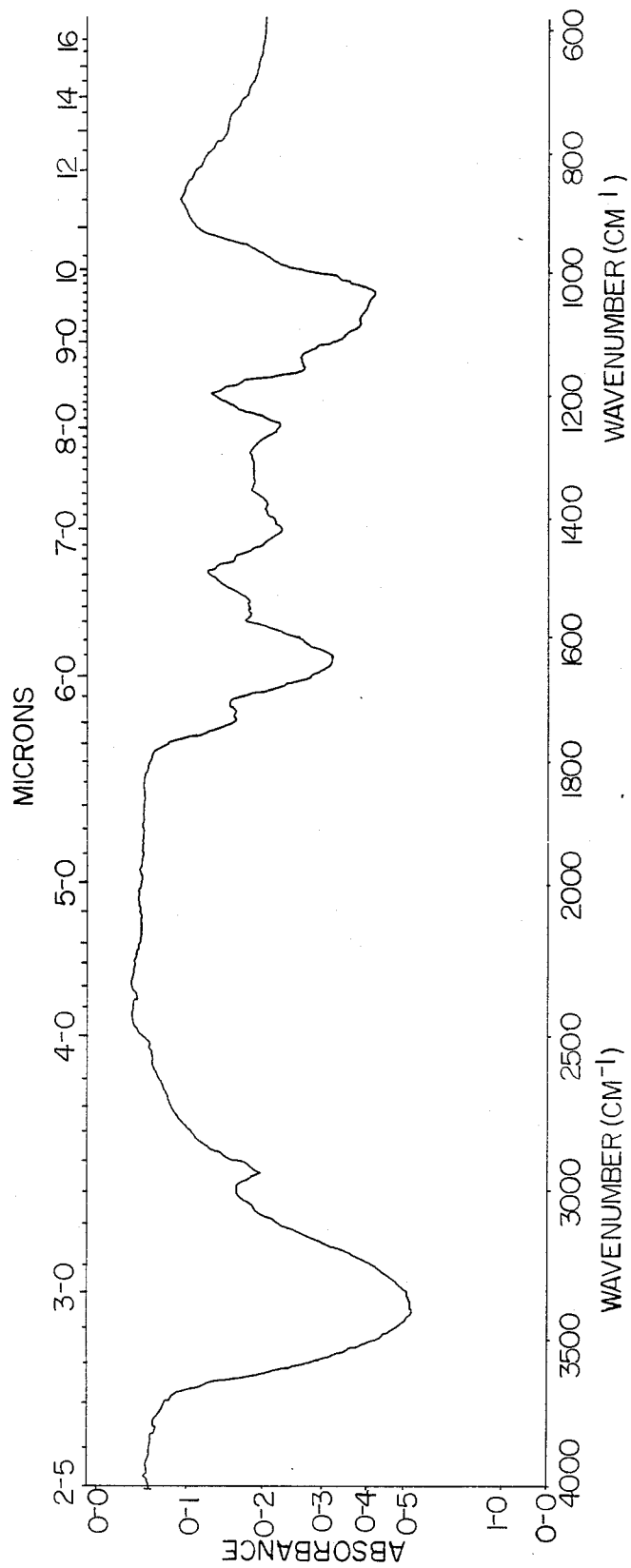
FIG. 3 shows an infrared curve of the antioxidant fraction A of the invention, isolated from spinach.
Figure 4:
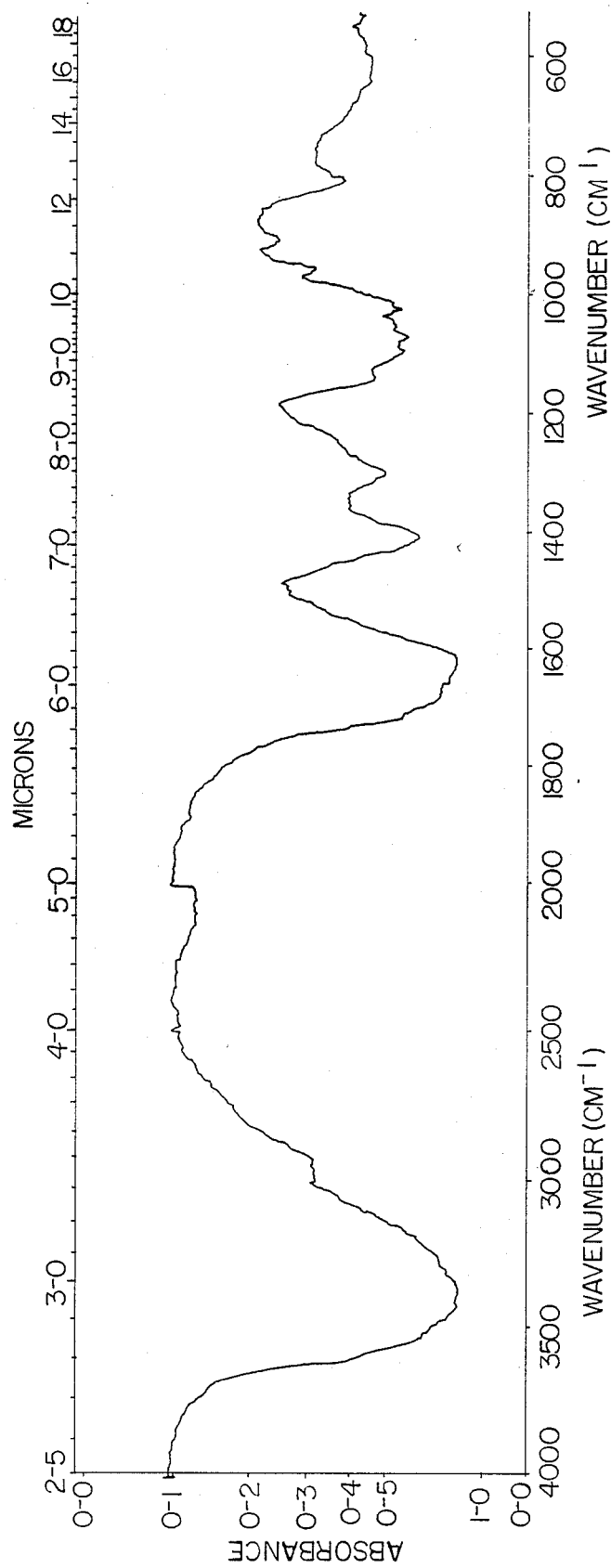
FIG. 4 shows an infrared curve of the antioxidant fraction B of the invention, isolated from spinach.
Figure 5:
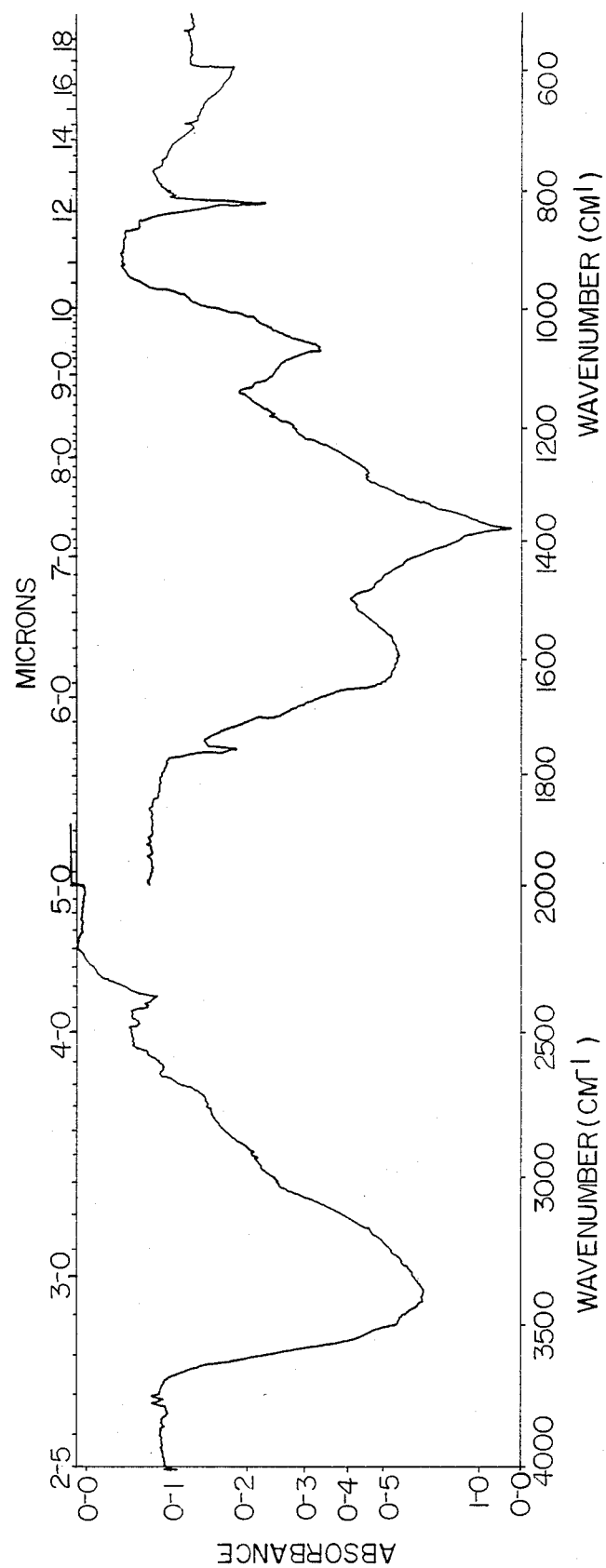
FIG. 5 shows an infrared curve of the antioxidant fraction C of the invention, isolated from spinach.
Figure 6:
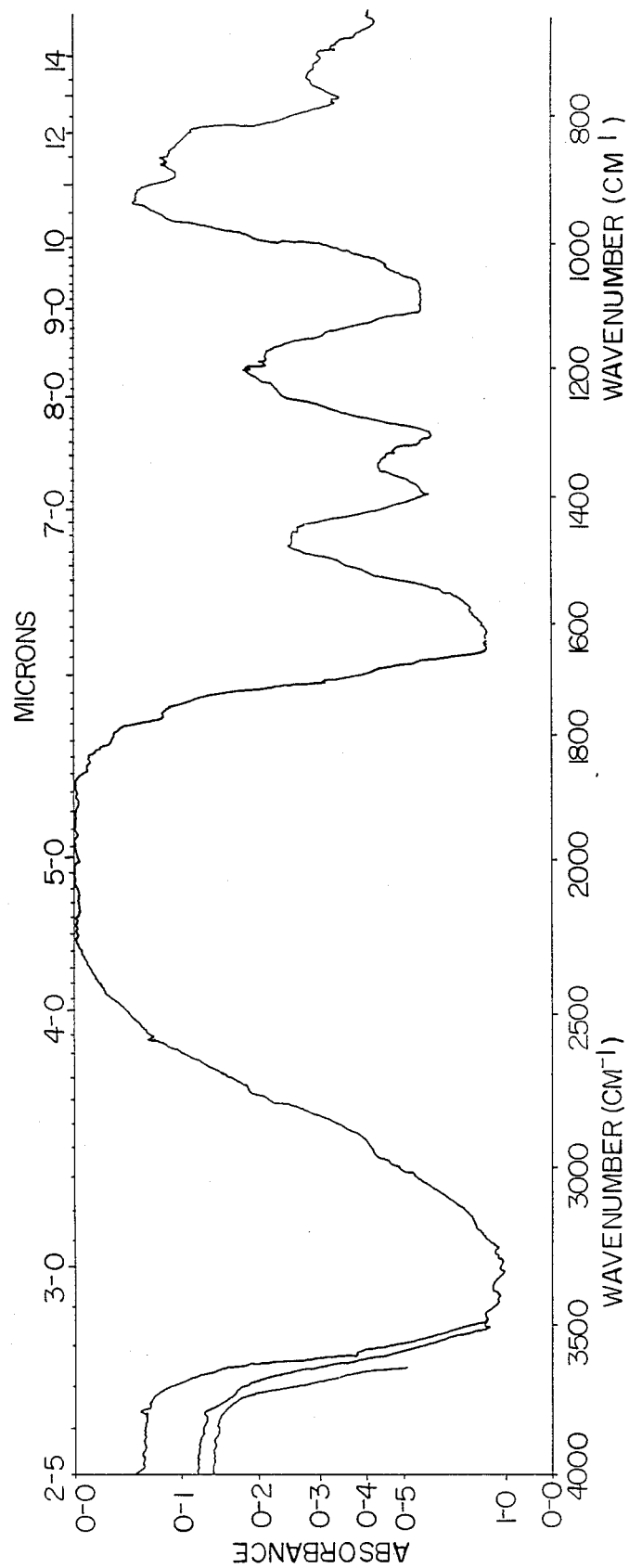
FIG. 6 shows an infrared curve of the antioxidant fraction $C_1$ of the invention, isolated from spinach.

The following infrared data was obtained from the spinach-derived fractions: A: (see FIG. 3) broad band at $3400 \text{ cm.}^{-1}$, strong bands at 1050 and $1650 \text{ cm.}^{-1}$, weak bands at 1250 and $1430 \text{ cm.}^{-1}$. B: (see FIG. 4) broad bands at 3400, 1640 and $1080 \text{ cm.}^{-1}$, additional bands at 1420, 1300 and $810 \text{ cm.}^{-1}$. C: (see FIG. 5) broad bands at 3400 and $1600 \text{ cm.}^{-1}$, strong band at $1390 \text{ cm.}^{-1}$, additional bands at 1070 and $820 \text{ cm.}^{-1}$. $C_1$: (see FIG. 6) broad band at $3300 \text{ cm.}^{-1}$, strong band at $1620 \text{ cm.}^{-1}$, additional bands at 1390, 1320, 1080 and $770 \text{ cm.}^{-1}$. $A_1$: (see FIG. 7) broad band at $3300-3400 \text{ cm.}^{-1}$, strong band at $1650 \text{ cm.}^{-1}$, additional bands at 1730, 1540, 1250 and $1080 \text{ cm.}^{-1}$, weak bands at 2920, 1400 and $1150 \text{ cm.}^{-1}$.

EXAMPLE 2

Samples of creams and appropriate controls were applied to mice or rat skin for a fixed period. The application was done once a day. Experiments were terminated by killing the animal, peeling the skin and freezing it in liquid nitrogen. Samples of the frozen skin were homogenized in 0.2.M phosphate buffer, pH 6.5. After centrifugation, the supernatant was collected and analyzed for the peroxide value using the TBA (thiobarbituric acid) test as described by Sinnhuber et. al, Food Res. 23: 620 (1958).

In the experiments which follow, newborn (hairless) rats were used. It is generally considered that the penetration through the skin of newborn rats is better than in adult rats, since at this stage they have not yet developed any fur.

TEST No. 1

In this experiment the control group was treated with Vaseline only, while the test group was treated with Vaseline containing a $C_1$ fraction. The test was run for 12 days and the results are presented in Table 1.

TABLE 1

| GROUP | TBA (O.D. 532/1 g. tissue) | Level of Peroxidation | P value* (n = 3) |
|---|---|---|---|
| Control | 0.295 | 100% | 0.002 |
| +0.5% $C_1$ | 0.188 | 64% | 0.002 |

*standard deviation

It is clearly demonstrated that the $C_1$ penetrates the skin of newborn rats and consequently reduces the level of peroxides in the skin. Since peroxides, and the free radicals involved in their formation and breakdown, constitute one of the main routes leading towards aging, the activity of this unique antioxidant can be considered as an anti-aging factor.

TEST No. 2

In this experiment the antioxidant was dissolved in Oil of Olay obtained in Israel (excellent solubility) and experiments similar to that described in No. 1 were performed. The results are presented in Table 2.

TABLE 2

| GROUP | TBA (O.D 532/1 g. tissue) | Level of Peroxidation | P value* (n = 4) |
|---|---|---|---|
| Control (no treatment) | 0.295 | 100% | 0.002 |
| Control (Oil of Olay) | 0.230 | 78% | 0.005 |
| +0.15% $C_1$ | 0.200 | 68% | 0.011 |
| +1.5% $C_1$ | 0.191 | 65% | 0.010 |

*standard deviation

As in test no. 1, the antioxidant significantly reduced the level of peroxides in the skin. It is interesting to point out that in newborn rats, Oil of Olay without the antioxidant also reduced the peroxide level. This may be attributed to the commercial antioxidants present in the Oil of Olay which was used. It is possible that in newborn skin, due to its relatively high permeability, small amounts of these antioxidants can also penetrate the skin. However, in adult mice or rats, as will be shown later, Oil of Olay did not reduce the level of peroxides in the skin. On the contrary, in general, a small increase in peroxide level was detected, which perhaps may be attributed to traces of metals in the cream.

EXAMPLE 3

In these experiments adult mice (2 months old) were treated as described in Example 2. The grown mice were shaved before applying the creams to the skin. In this experiment the antioxidant was dissolved in Oil of Olay. Mice were sacrificed after 21 days. The results are presented in Table 3.

TABLE 3

| GROUP | TBA (O.D. 532/1 g. tissue) | Level of Peroxidation | P value* (n + 3) |
|---|---|---|---|
| Control (no treatment) | 0.338 | 100% | 0.019 |
| Control (Oil of Olay) | 0.400 | 118% | 0.026 |
| +0.3% $C_1$ | 0.240 | 71% | 0.002 |

*standard deviation

It seems that in grown mice the Oil of Olay slightly increases the level of peroxides while addition of the antioxidant at a concentration of 0.3% significantly reduced these peroxides, thus indicating that even with grown mice the antioxidant penetrates the skin. We would like to point out that in similar experiments when we tried the effect of 0.1% BHT, BHA and alpha tocopherol dissolved in Oil of Olay on the level of peroxides in the skin, no reduction of the level of peroxides was observed.

EXAMPLE 4

A new model for studying aging was developed. The new model involves the exposure of adult shaved mice to a UV lamp (sun lamp 300 W) for a short period. As a result, the aging processes as expressed by the level of peroxidation are stimulated and the effect of the natural antioxidant was studied. Using this new technique, the optimal antioxidant dose for the inhibition of aging was determined. In this experiment, a crude preparation of antioxidant (and not the final purified antioxidant) was used.

Adult mice were shaved and the individuals were exposed to the UV light (Philips HP 3115), with or without antioxidant, for a short period of one minute for two days (two exposures in total). On the third day they were sacrificed and the level of peroxidation in the skin was determined by the TBA (thiobarbituric acid) test. Controls without exposure to the UV light were also included. Antioxidant was dissolved in Oil of Olay. The results are presented in Table 4.

TABLE 4

Effect of antioxidant dose on aging (7 individuals in each group)

| | GROUP | TBA (O.D. 532/ 1 g. tissue | Level of Peroxidation | P value* (n = 7) |
|---|---|---|---|---|
| 1. | no radiation | 0.147 | 16.7% | 0.010 |
| 2. | radiation + Oil of Olay | 0.880 | 100% | 0.027 |
| 3. | radiation + 0.3% antioxidant in Oil of Olay | 0.740 | 84% | 0.006 |
| 4. | radiation + 0.4% antioxidant in Oil of Olay | 0.680 | 77% | 0.020 |
| 5. | radiation + 0.5% antioxidant in Oil of Olay | 0.680 | 77% | 0.011 |
| 6. | radiation + 1.0% antioxidant in Oil of Olay | 0.700 | 79% | 0.006 |

*standard deviation

The optimal dose of crude antioxidant to be used is 0.3 to 0.4%.

EXAMPLE 5

Samples of human skin were obtained from a Plastic Surgery Department of a hospital. These samples were placed in a saline solution immediately after their removal from the patients.

The skin samples were exposed to UV rays (Philips Sun Lamps) for 5 minute intervals, three successive times with a 5 minute rest period between each exposure. The distance between the lamp and the tissue was 12 cm. The skin samples were stored for 3 days at 4° C., after which time they were peeled and homogenized. 20-30 mg. of peeled tissue were assayed for peroxide level using the spectrophotometric TBA test.

The results clearly demonstrate that the peroxide level (aging) of the skin tissue was raised due to the exposure to UV rays. Skin treated with the antioxidant of the invention and exposed to Uv rays for the same period of time showed a peroxide level similar to the untreated control. These results are shown in Table 5.

TABLE 5

| Sample | TBA (O.D. 532/ 0.1 g. tissue) | Level of Peroxidation |
|---|---|---|
| Unexposed | 0.050 | 62.5% |
| Exposed | 0.080 | 100% |
| Exposed + Oil of Olay | 0.100 | 125% |
| Exposed + (A + B + C) + Oil of Olay | 0.050 | 62.5% |

The experiments run on human skin indicate the following:

(a) the antioxidant penetrates the skin;

(b) the antioxidant significantly reduces the level of peroxides.

It is noted that when a mixture of fractions A+B+C was used, an effective antioxidant result was observed.

EXAMPLE 6

The crude extract was tested in vivo for its effect on the immune response system in experimental mice. In these experiments, male Balb-C mice were injected intraperitoneally with 1 mg. of the crude extract from *Spinacia oleracea* per 0.2 ml. of phosphate buffer solution (PBS) per animal. Animals were sacrificed one, three and seven days after injection, following which their spleens were removed. Spleen cells ($10^7$ cells/ml. enriched RPMI) were cultured for 24 hours in the presence of CON A (concavalin-A) 2 ug./ml. and the supernatants thus obtained were tested for both IL-2 (interleukin-2) and CSF (colony stimulating factor). No significant differences were found between controls (i.e. animals receiving no treatment) and experimental animals, in their ability to produce IL-2 as well as CSF, indicating that the antioxidant has no adverse effect on the immune system. In addition, no pathological findings were observed in injected animals.

Additional testing determined that a single dose of 25 mg./mouse i.p. may be tolerated and that the $LD_{50}$ is in the range of 1400 mg./kg. for mice.

EXAMPLE 7

The $C_1$ fraction was dissolved in PBS (50 mg./10 ml.) and 0.2 ml. of this solution was injected i.p. into each mouse twice weekly. The $C_1$ fraction was also administered orally in an aqueous solution (1 mg./ml.) and the mice were allowed to drink the solution from a calibrated bottle to enable measurement of the quantity of the $C_1$ fraction consumed by each individual mouse to be determined. Each mouse was subsequently injected with 0.6 mg. methylcholanthrene, a known inducer of fibrosarcoma. Test series A and B were carried out as follow, in which the figures refer to number of animals in which the appearance of tumors occurred/the number of animals in the group:

TABLE 6

| Weeks after innoculation with methylcholanthrene | Controls | Groups treated with Cl antioxidant | |
|---|---|---|---|
| | | Orally | i.p. |
| (TEST A) | | | |
| 5 | 4/20 | 1/10 | 1/10 |
| 6 | 9/20 | 1/10 | 1/10 |
| 7 | 14/20 | 3/10 | 2/10 |
| 8 | 16/20 | 3/10 | 2/10 |
| 9 | 18/20 | 4/10 | 2/10 |
| (TEST b) | | | |
| 7 | 1/10 | 0/8 | 0/9 |
| 8 | 3/10 | 0/8 | 0/9 |
| 9 | 4/10 | 0/8 | 0/9 |
| 10 | 4/10 | 0/8 | 0/9 |
| 11 | 6/10 | 1/8 | 0/9 |
| 12 | 7/10 | 1/8 | 0/9 |
| 13 | 7/10 | 2/8 | 1/9 |

At week 13 (test B), after as many as 25-29 injections, one mouse frome ach group was sacrificed and observed for gross internal changes (i.e. lymph nodes, spleen, liver, kidney, heart and lung, etc.): no significant changes and no pathological damage were observed. This demonstrated that even a prolonged treatment with the $C_1$ fraction by different routes of administration did not cause any damage to the treated mice.

The in vivo experiments demonstrated that i.p. or oral administration with $C_1$ is effective in delaying the apperance and reducing the frequency of methylcholanthrene-induced tumors.

EXAMPLE 8

Skin tests on human volunteers using a 0.3% w/w dispersion of the crude extract in Oil of Olay have resulted in subjective improvement in the texture of the skin with no adverse effects in any test subjects.

EXAMPLE 9

This example is illustrative of compositions which may be used in the practice of the invention.

| Lotion | |
|---|---|
| Antioxidant | 1.0 g. |
| Base* | 99.0 g. |
| | 100.0 g. |
| *stearic acid | 1.4 g. |
| triethanolamine | 0.6 g. |
| glyceryl monostearate | 4.0 g. |
| lanolin, hydrous | 1.0 g. |
| cetyl alcohol | 0.4 g. |
| mineral oil | 2.0 g. |
| methyl parahydroxybenzoate | 0.1 g. |
| distilled water | 90.5 g. |
| (+ perfume) | |
| | 100.0 g. |
| Cream | |
| antioxidant | 1.0 g. |
| cetyl alcohol | 0.4 g. |
| stearyl alcohol | 7.4 g. |
| isopropyl myristate | 2.0 g. |
| sodium lauryl sulfate | 1.4 g. |
| white petrolatum | 27.6 g. |

| | |
|---|---|
| propylene glycol | 9.2 g. |
| water, to make | 100.0 g. |

EXAMPLE 10

Figure 2:
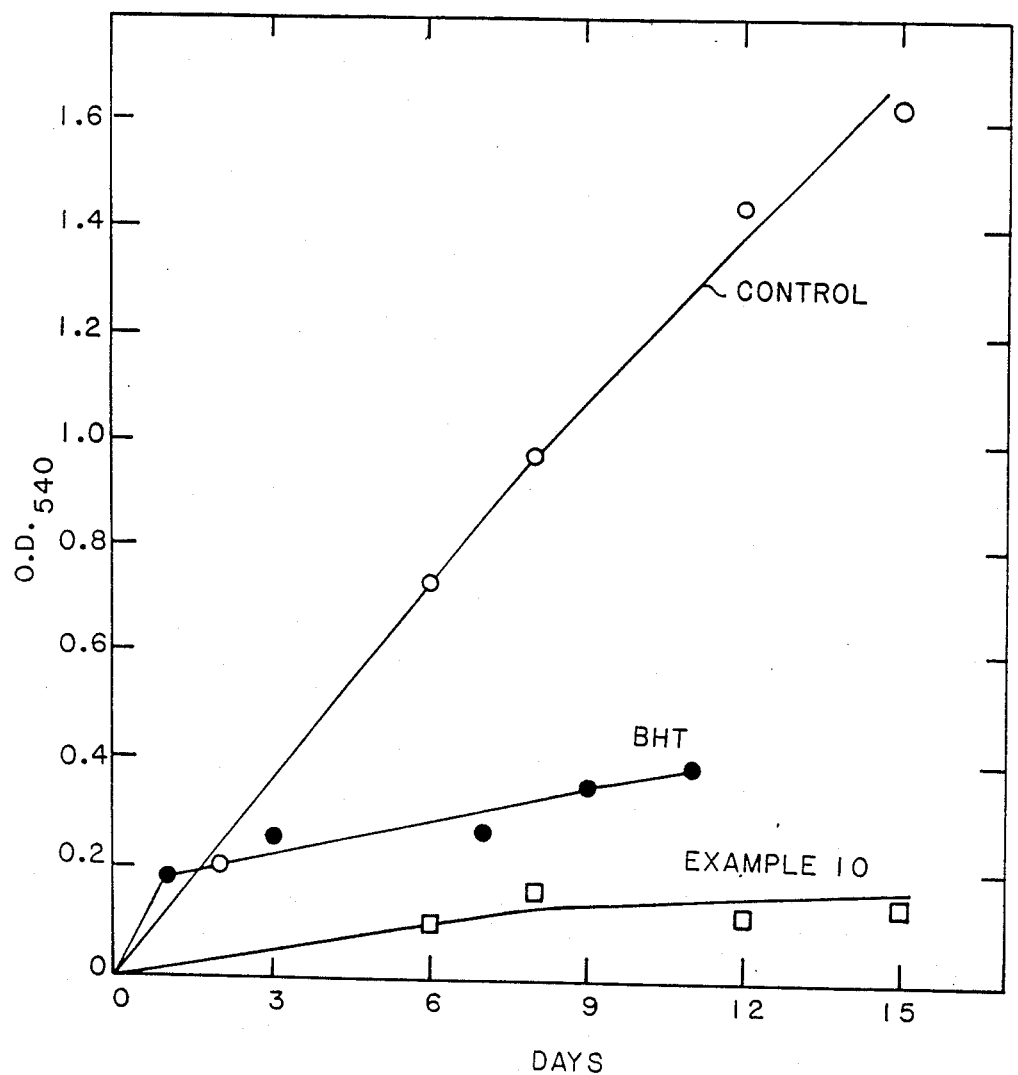
FIG. 2 shows a graphical comparison of the antioxidant effect of the composition of the invention with BHT.

The crude antioxidant (A, B and C) was added to linoleic acid to form a mixture containing 20 ml. of $7.5 \times 10^{-3}$M linoleic acid in 0.2M aqueous sodium phosphate buffer (ph 6.5), containing 0.25% Tween 20 (R) and 1 mg. of the crude antioxidant. Controls were run which contained the buffer and Tween 20 but no antioxidant, as well as a sample of linoleic acid with 1 mg. of BHT and the same dispersant system. The mixture was kept at 30° C. and the optical density was determined using the ferric thiocyanate method describe by R. B. Koch et. al. in Arch. Biochem. Biophys. 78: 165 (1959). The test results depicted in FIG. 2 show that the antioxidant of the invention is more effective than BHT in preventing oxidation of linoleic acid.

EXAMPLE 11

Isolation of antioxidant materials from clover

A similar procedure to that described for spinach, was applied to isolate antioxidant materials from clover (*trifolium alexandrinum*). The crude extract was separated on Sephadex G-25 to give fractions A, B and C. Fraction A was purified on Ecteola to give fraction $A_1$. Fraction C ws resolved on Sephadex G-10 to give fractions $C_1$ and $C_2$. Fraction $C_1$ was further resolved by dissolving in a minimum amount of water, applying to 0.2 mm. silica gel plates and developing in 30:60 v/v $H_2O$-athanol, to give fractions labelled TLC-1, -2 and -3.

Figure 8:
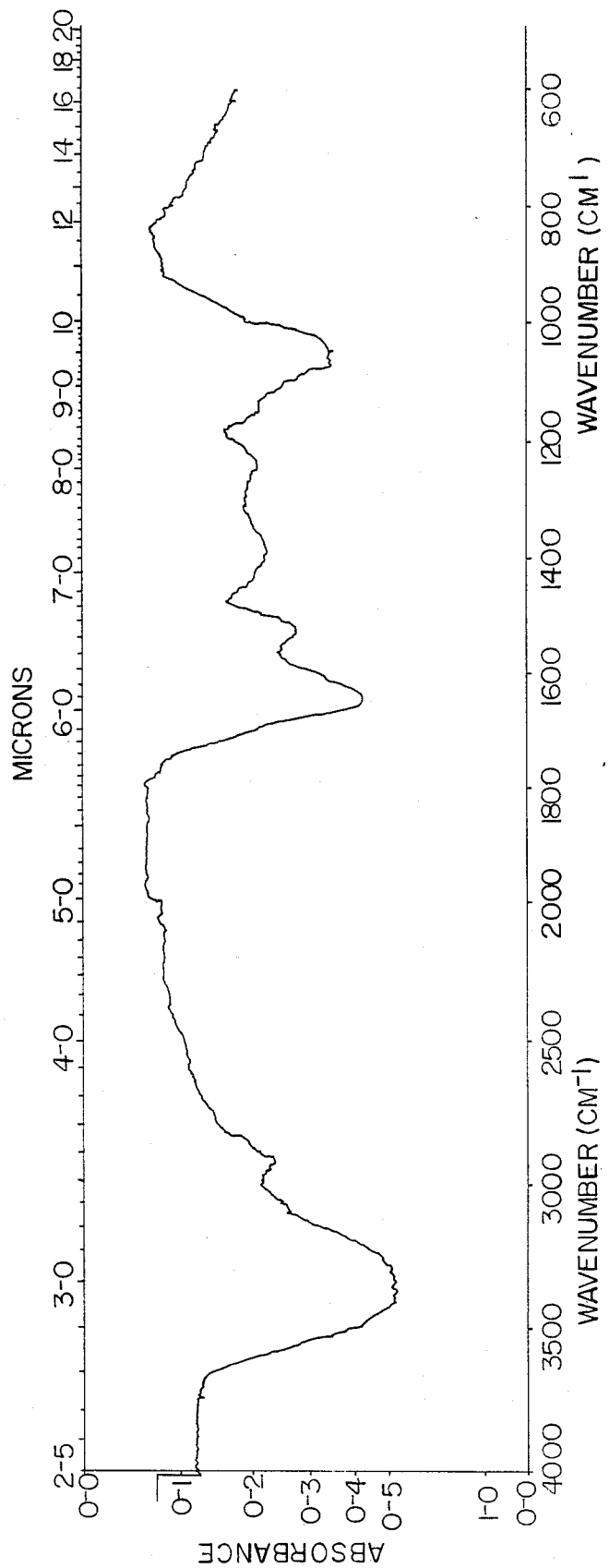
FIG. 8 shows an interest curve of the antioxidant fraction A of the invention, isolated from clover.

The following infrared data was obtained:

A: (see FIG. 8) similar to the analogous spinach fraction.

Figure 9:
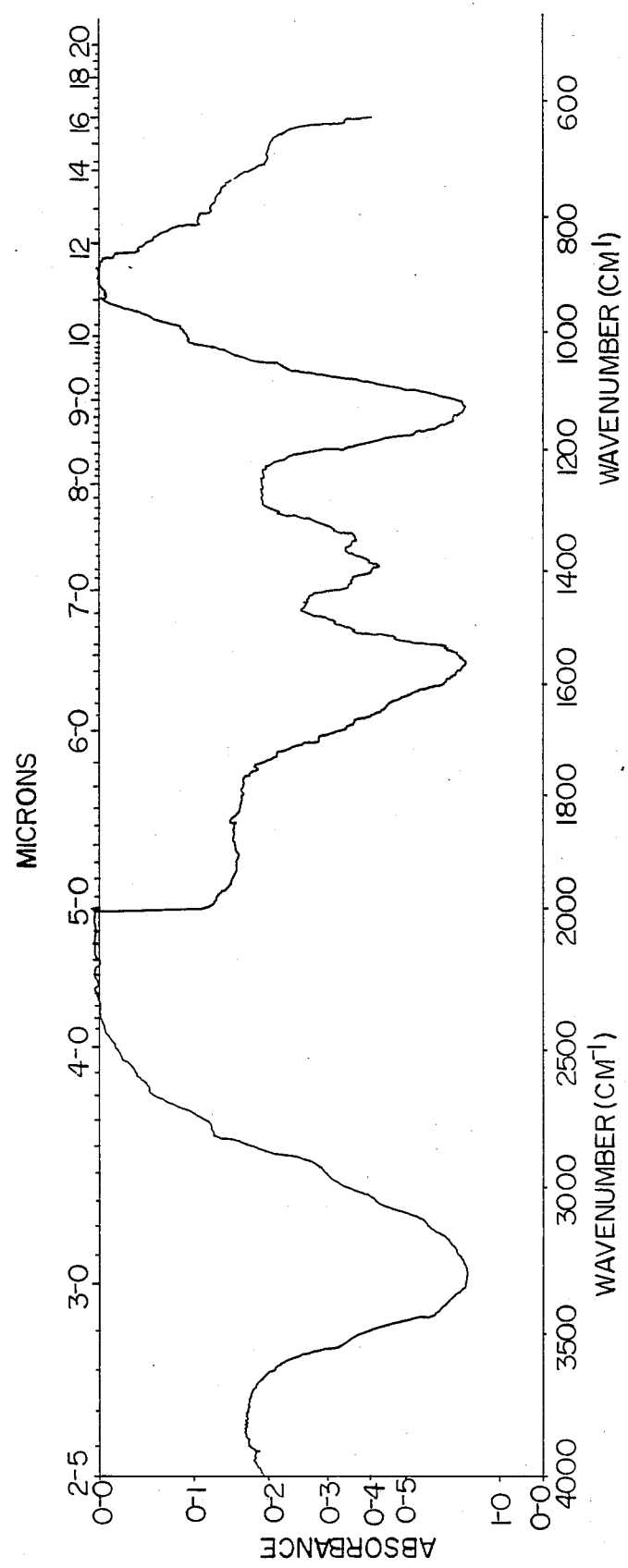
FIG. 9 shows an infrared curve of the antioxidant fraction B of the invention, isolated from clover.

B: (see FIG. 9) strong and broad bands at 3300, 1560 and 1130 cm.$^{-1}$, medium band at 1400 cm.$^{-1}$, weak bands at 1350 and 1430 cm.$^{-1}$.

Figure 10:
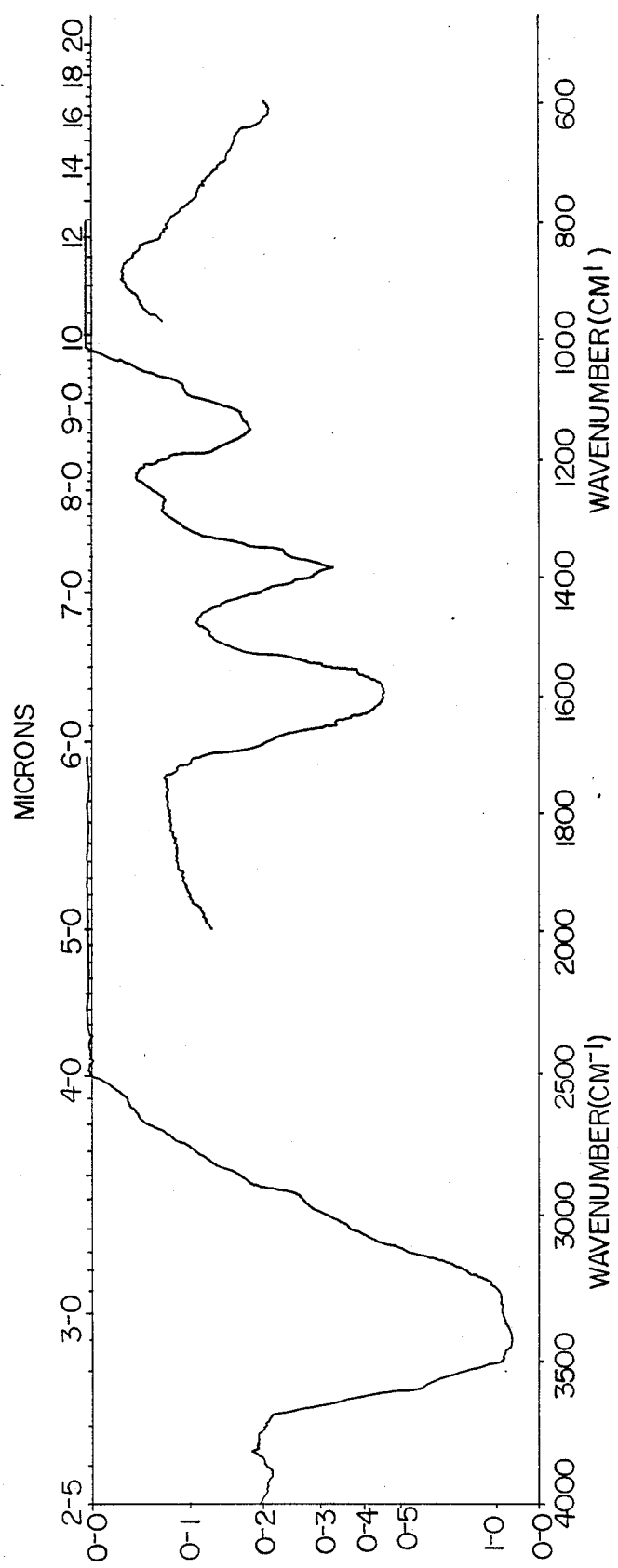
FIG. 10 shows an infrared curve of the antioxidant fraction C of the invention, isolated from clover.

C: (see FIG. 10) broad band at 3430 cm.$^{-1}$, strong bands at 1600, 1380 and 1150 cm.$^{-1}$.

Figure 11:
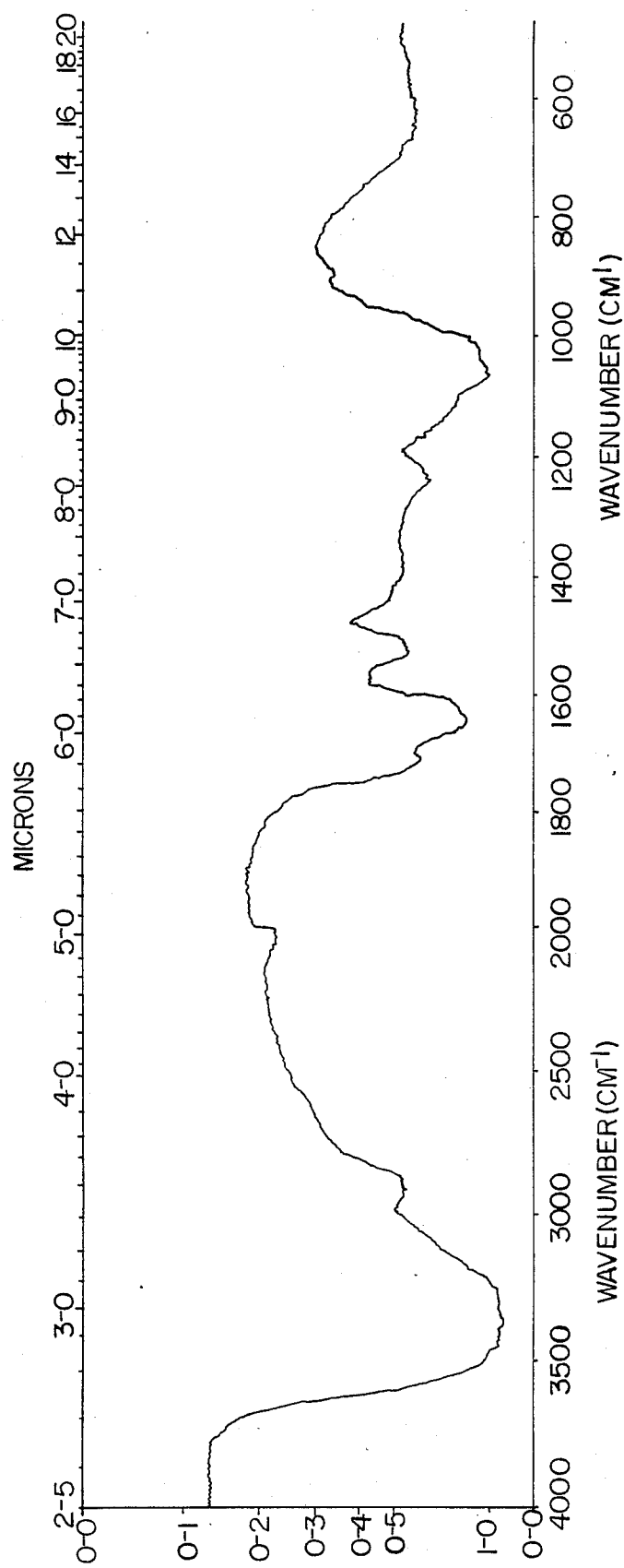
FIG. 11 shows an infrared curve of the antioxidant fraction $A_1$ of the invention, isolated from clover.

$A_1$: (see FIG. 11) similar to the analogous spinach fraction.

Certain of the foregoing fractions (0.2 mg. in each case) derived from clover were tested as antioxidant in a system which contained linoleic acid as substrate and the enzyme lipoxygenase as catalyst. Oxygen absorption was followed using an oxygen monitor according to Grossman and Zakut, in Methods of Biochemical Analysis (D. Glick, Ed.) 25: 303-29 (1979). The results are shown in Table 7.

TABLE 7

| Inhibition of Lipid Peroxidation by Antioxidants from Clover. | |
|---|---|
| Fraction | % Inhibition |
| crude extract | 20 |
| A | 9 |
| B | 16 |
| C | 30 |
| TLC-1 | 42 |
| TLC-3 | 46 |

EXAMPLE 12

Isolation of antioxidant materials from algae

A number of algae samples were homogenized with distilled water and an extract was prepared according to the technique described above for spinacia oleracea. The crude homogenate was centrifuged, and the supernatant was collected and dried by lyophilization. The dried crude extracts were tested as antioxidants in a system which contained linoleic acid as a substrate and enzyme lipoxygenase as catalyst. Oxygen absorption was followed using an oxygen monitor according to Grossman and Zakut, in Methods of Biochemical Analysis (D. Glick, Ed.) 25: 303-29 (1979). The results in Table 8 wre obtained using 2.5 mg. crude extract.

TABLE 8

| Inhibition of Lipid Peroxidation by Antioxidants from Algae. | |
|---|---|
| Algae | % Inhibition |
| Spirulina | 30 |
| Nicractinium | 27 |
| Synichococcus | 30 |
| Navicola | 42 |
| Euglena | 35 |
| Red | 35 |

While the invention has been described above with respect to its presently preferred embodiments, it will be apparent to those skilled in the art that many variations and modifications may be made. The invention is accordingly not to be construed as restricted to the illustrated embodiments, rather its scope will be defined in the claims which follows.

We claim:

1. A water soluble antioxidant material prepared from plant tissue, and fractions separable from said water soluble antioxidant material by chromatography, wherein said tissue is obtained from a plant of the Order Chenopodiales said antioxidant having the following characteristics; namely:
   (a) it is stable for an extended period of time, at least in the dry state, at ambient temperature and pressure;
   (b) it is absorbed through the skin;
   (c) it lowers the peroxide level of the skin.

2. A material according to claim 1, wherein said tissue is obtained from a member selected from the group consisting of Chenopodiaceae and Aizoaceae.

3. An antioxidant material according to claim 2, wherein the said plant tissue is constituted by plant tissue selected from the group consisting of fresh leaves and stems.

4. An antioxidant material according to claim 3 wherein said extracts are chromatographically separable on dextran which has been cross-linked with epichlorohydrin and has a pore size of 50-150 um, into fractions which are colored brown(A), yellow(B) and orange(C), and of which fraction A is chromatographically purifiable on a substance which is either (1) a condensation product of cellulose with epichlorohydrin and triethanolamine having a capacity of 0.3 to 0.4 meg./g and a particle size 0.05-0.2. mm. or (ii) dextran which has been cross-linked with epichlorohydrin and has a pore size of 40-120 um, to give a fraction ($A_1$) having an infrared spectrum with substantially the following features: broad band at 3300-3400 cm.$^{-1}$, strong band at 1650 cm.$^{-1}$, additional bands at 1730, 1540, 1250 and 1080 cm.$^{-1}$, weak bands at 2920, 1400 and 1150 cm.$^{-1}$, and fraction C being chromatographically separable on dextran which has been cross-linked with epichlorohydrin and has a pore size of 40-120 um, into fractions colored dark brown and yellow orange, and labelled $C_1$ and $C_2$ respectively.

5. An antioxidant material which comprises at least one substance selected from the group consisting of fractions A, $A_1$, B, $C_1$ and $C_2$, as defined in claim 4.

6. An antioxidant material which comprises a combination of at least two substances selected from the group consisting of fractions A, $A_1$, B, $C_1$ and $C_2$, as defined in claim 4.

7. An antioxidant material as defined in claim 2 which is obtained from *Spinacia oleracea.*

8. An antioxidant material as defined in claim 2 which is obtained from *Antriplex hortensis.*

9. An antioxidant material as defined in claim 2 which is obtained from *Tetragonia expansa.*

10. An antioxidant material characterized by stability for an extended period of time at ambient temperature and pressure, at least in the dry state, which is obtained by extraction of plant tissue from plants of the families selected from the group consisting of Chenopodiaceae and Aizoaceae with water and subsequent fractionation by chromatographic methods, and having an infrared spectrum with substantially the features states in any one of the following paragraphs (a) to (g), namely:
  (a) broad band at 3400 cm.$^{-1}$, strong bands at 1050 and 1650 cm.$^{-1}$, weak bands at 1250 and 1430 cm.$^{-1}$;
  (b) broad bands at 3400, 1640 and 1080 cm.$^{-1}$, additional bands at 1420, 1300 and 810 cm.$^{-1}$;
  (c) broad bands at 3400 and 1600 cm.$^{-1}$, strong band at 1390 cm.$^{-1}$, additional bands at 1070 and 820 cm.$^{-1}$;
  (d) broad band at 3300 cm.$^{-1}$, strong band at 1620 cm.$^{-1}$, additional bands at 1390, 1320, 1080 and 770 cm.$^{-1}$;
  (e) broad band at 3300-3400 cm.$^{-1}$, strong band at 1650 cm.$^{-1}$, additional bands at 1730, 1540, 1250 and 1080 cm.$^{-1}$, weak bands at 2920, 1400 and 1150 cm.$^{-1}$;
  (f) strong and broad bands at 3300, 1560 and 1130 cm.$^{-1}$, medium band at 1400 cm.$^{-1}$, weak bands at 1350 and 1430 cm.$^{-1}$;
  (g) broad band at 3430 cm.$^{-1}$, strong bands at 1600, 1380 and 1150 cm.$^{-1}$.

11. A composition of matter for cosmetic use, which comprises a stable antioxidant material as defined in claim 1 together with an inert diluent or carrier.

12. A composition according to claim 11, wherein the inert diluent or carrier is adapted for application to the skin.

13. A composition according to claim 12, wherein the inert diluent or carrier is cosmetically acceptable.

14. A composition according to either claim 11 or claim 16, wherein said composition contains from about 0.005 to about 5% by weight of said antioxidant material, based upon the total weight of the composition.

15. A composition according to any of claims 12 to 14, wherein said composition is in the form of a hydrophilic cream, a hydrophilic lotion, a hydrophobic cream or a hydrophobic lotion.

16. A composition according to claim 15 which further comprises a local anaesthetic.

17. A composition according to claim 11, wherein the inert diluent or carrier is adapted for oral, rectal or parenteral administration.

18. A composition according to claim 17, wherein said stable antioxidant material is present in an amount such that the composition is suitable for the administration of about 20 to about 500 mg. said material per kg. weight of a subject.

19. A process for preparing a stable antioxidant material as defined claims 1, 2, 3, 4, 5, 6 or 7, which comprises the steps of extracting plant tissue with water, comminuting said tissue prior to or simultaneously with the extracting step and there after chromatographically separating said water soluble antioxidant material.

20. A process according to claim 19, wherein said comminution is effected at a temperature within the range of from about 4° to about 100° C.

21. A process according to claim 20, wherein said temperature is about 25° C.

22. A process according to claim 8, which comprises chromatographically separating said extract on dextran which has been cross-linked with epichlorohydrin and has a pore size of 50-150 um, into fractions which are colored brown(A), yellow(B) and orange(C), and effecting at least one of the following chromatographic purifications on said fractions, namely:
  chromatographically purifying fraction A on a condensation product of cellulose with epichlorohydrin and triethanolamine having a capacity of 0.3 to 0.4 meg./g and a particle size 0.05-0.2 mm., or on dextran which has been cross-linked with epichlorohydrin and has a pore size of 40-120 um, to give a fraction($A_1$) having substantially the following IR spectrum:
    broad band at 3300-3400 cm.$^{-1}$,
    strong band at 1650 cm.$^{-1}$,
    additional bands at 1730, 1540, 1250 and 1080 cm.$^{-1}$,
    weak bands at 2930, 1400 and 1150 cm.$^{-1}$;
  chromatographically separating fraction C on dextran which has been cross-linked with epichlorohydrin and has a pore size of 40-120 um, into fractions colored dark brown and yellow orange, and labelled $C_1$ and $C_2$ respectively.

23. A stable antioxidant material, which has been prepared by the process according to claim 8.

24. A method for cosmetically enhancing the texture of the skin, which method comprises applying to the skin a composition according claim 15.

* * * * *